United States Patent [19]
Kenyon et al.

[11] Patent Number: 6,004,743
[45] Date of Patent: Dec. 21, 1999

[54] METHOD AND APPARATUS FOR BULK ENRICHMENT OF A POPULATION OR SUBPOPULATION OF CELLS

[76] Inventors: Norma S. Kenyon, 8020 SW. 151 St., Miami, Fla. 33158; Thomas R. Russell, 14000 SW. 111 St., Miami, Fla. 33186; Camillo Ricordi, 72 S. Hibiscus Dr., Hibiscus Island, Miami Beach, Fla. 33139; Robert K. Zwerner, 4811 SW. 133 Ave., Fort Lauderdale, Fla. 33330

[21] Appl. No.: 08/989,124

[22] Filed: Dec. 10, 1997

Related U.S. Application Data

[63] Continuation of application No. 08/558,268, Nov. 13, 1995, abandoned.

[51] Int. Cl.$^6$ ............................ A01N 1/02; G01N 33/567
[52] U.S. Cl. ........................ 435/2; 435/7.21; 435/7.23; 435/7.24; 435/7.25; 435/372; 435/372.1; 435/372.2; 435/372.3; 210/515; 436/523
[58] Field of Search .................. 435/2, 7.21, 7.23–7.25, 435/372, 372.1–372.3; 210/222, 515, 695; 436/523, 525, 526, 824

[56] References Cited

U.S. PATENT DOCUMENTS

| | | |
|---|---|---|
| 3,928,143 | 12/1975 | Coughlin et al. .................. 435/147 |
| 4,115,535 | 9/1978 | Giaever . |
| 4,487,700 | 12/1984 | Kanter . |
| 4,752,563 | 6/1988 | Kortright et al. . |
| 4,910,148 | 3/1990 | Sorenson et al. . |
| 5,137,809 | 8/1992 | Loken et al. . |
| 5,229,268 | 7/1993 | Pry et al. . |
| 5,238,812 | 8/1993 | Coulter et al. . |
| 5,256,532 | 10/1993 | Melnicoff et al. . |
| 5,474,687 | 12/1995 | Van Vlasselaer . |
| 5,576,185 | 11/1996 | Coulter et al. . |

FOREIGN PATENT DOCUMENTS

| | | |
|---|---|---|
| WO 95/28643A | 10/1995 | WIPO . |

OTHER PUBLICATIONS

Reynolds et al. Cancer Research, vol. 46, pp. 5882–5888, 1986.
Kessler et al. Blood Suppl. vol. 1, p. 321a, 1987.
Falkenburg et al. Exp. Hematol. vol. 14, pp. 101–105, 1986.
Stem Cell Technologies Inc., Price list and brochure—undated.

*Primary Examiner*—Leon B. Lankford, Jr.
*Assistant Examiner*—Christopher R. Tate
*Attorney, Agent, or Firm*—Cooley Godward LLP

[57] ABSTRACT

A cell population or subpopulation enrichment procedure for separating undesired populations or subpopulations from a biological sample utilizing relatively heavy, dense particles and gravity sedimentation. The particles have one or more reactants bound thereto which are specific to and will bind with the selected population or subpopulation to be eliminated from the sample. The particles preferably are mixed with the sample by repeatedly causing the particles to settle through a substantial portion of the sample to bind to the selected population. The particles with the bound selected population to be eliminated then are allowed to preferentially settle in the sample and the supernatant including the enriched population or subpopulation is separated from the particles with the population to be eliminated bound thereto. The enriched population supernatant can then be analyzed, utilized as is, have other populations or subpopulations removed or have additional amounts of remaining cells of the previously eliminated populations removed in additional steps.

38 Claims, 12 Drawing Sheets

FIG. 3A　　　　　　　　　　　　　FIG. 3B

METHOD AND APPARATUS FOR BULK ENRICHMENT OF A POPULATION OR SUBPOPULATION OF CELLS

This application is a continuation of U.S. application Ser. No. 08/558,268, filed Nov. 13, 1995, now abandoned.

BACKGROUND OF THE INVENTION

This invention relates generally to the enrichment of one or more desired populations or subpopulations from a sample having a plurality of cell populations to obtain the desired populations or subpopulations alone or the enriched populations or subpopulations with other populations, but with one or more undesired subpopulations removed therefrom. More particularly, the invention is directed to enriching the desired population or subpopulation such as cells from bone marrow, vertebral body marrow, or blood, by binding undesired populations or subpopulations to relatively dense particles and utilizing gravity sedimentation to separate the undesired populations or subpopulations from the remaining sample supernatant containing the enriched populations or subpopulations.

The enhancement or enrichment of a population or a subpopulation of a sample can be utilized for many types of applications. The pluripotent hematopoietic stem cell (HSC) population, which originates from the bone marrow, gives rise to all the red blood cells (RBC's) and white blood cells (WBC's) of the human body. These cells constitute a low percentage of the bone marrow (1–3%) and peripheral blood (<1%), and as for any rare event cell type, it is difficult to study the HSC population without first enriching for the population. Both experimentally and clinically, it has become highly desirable to enrich for and/or isolate the HSC population, which population is identified via cell surface expression of the CD34 antigen. The HSC population is also referred to hereinafter as the CD34 population.

The potential applications for the HSC population include, but are not limited to, bone marrow transplantation for: treatment of hematologic malignancies, such as leukemia and lymphoma; treatment of solid tumors, such as breast and ovarian cancer; enhancement of graft acceptance and induction of donor specific tolerance in recipients of solid organ or cellular transplants; amelioration or cure of autoimmune syndromes, such as insulin dependent diabetes mellitus and systemic lupus erythematosus; and cure of inborn errors of metabolism. In addition, purified stem cells are required for many gene therapy protocols, which may eventually be utilized to treat all of the above conditions. The ability to isolate the HSC population will also allow for the expansion of the pluripotent HSC population and desired subpopulations of the HSC population, such as precursor dendritic cells, which can subsequently be utilized in all of the above applications. With the advent of techniques which allow for successful bone marrow transplantation between genetically disparate individuals, isolation of the HSC population from the peripheral blood or bone marrow of normal volunteers, followed by expansion, cryopreservation, and banking of the cells for utilization in various clinical protocols will soon be possible. Isolation and cryopreservation, of the HSC population from human cord blood at birth can allow for preservation of that individual's cells which then can be employed for the treatment of multiple disorders should they arise in that individual's lifetime.

Many prior art techniques have been developed for the enrichment/isolation of the HSC population, all of which require removal of mature RBC's, which can interfere with freezing and thawing of marrow cells and which can also interfere with certain chemical purging techniques, utilized to eliminate tumor cells from the marrow inoculum. The vast majority of the prior art HSC population enrichment protocols involve the use of density gradient centrifugation over ficoll-paque or other gradient materials, in order to enrich for mononuclear cells and eliminate mature RBC's. Alternative prior art techniques of obtaining mononuclear cell preparations include utilization of specialized blood cell processors which result in concentration of the mononuclear white blood cells. Furthermore, after enrichment for mononuclear cells and removal of mature RBC's, the total percentage of CD34 positive HSC in the processed population is still only on the order of 1–3%, and further processing must be undertaken in order to enrich for the HSC population. Both positive and negative selection techniques have been employed to enrich for the HSC population. Positive selection for the HSC population has been accomplished by exploiting CD34 specific monoclonal antibodies, avidin and biotinylated anti-CD34, or anti-mouse immunoglobin specific polyclonal antibody and murine anti-CD34 (bound to flasks, columns, particles/beads, or some other substrate) to pull out the HSC population. Negative selection techniques employ monoclonal antibodies which can bind to lineage specific markers, not present on the HSC population, to specifically remove the non-HSC population. All of these procedures are time consuming, unwieldy, and costly. In addition, due to the extensive manipulation of the HSC population, cell recovery of the desired HSC population is low.

Currently, following gradient processing, several prior art enrichment approaches involve the utilization of a plurality of magnetic microspheres particles/beads, typically formed of a polymer based magnetic material of a relatively low density. Unlike the present invention, described hereinafter, these microspheres are selected to be of a relatively low density, because the microspheres are mixed with the bone marrow or blood and specifically are designed not to settle out by gravity sedimentation. The microspheres are typically of a small size, generally about or less than one micron in diameter. However, one product sold by Dynal, Inc. of Great Neck, N.Y., utilizes magnetic polymeric microspheres having a nominal diameter of 2.8 or 4.5 microns with a low microsphere density on the order of 1.5 gm/cc. The prior art magnetic microspheres are intended to be maintained in suspension in the sample and consequently are designed for very slow or substantial elimination of gravity settling in the sample suspension.

The magnetic microspheres have at least one antibody bound thereto specific to the population or subpopulation desired to be removed. Often, such as in the Dynal process, a first monoclonal antibody is bound to the cells of interest and a second antibody specific to the first monoclonal antibody is bound to the microspheres. The cells typically are isolated from whole blood or bone marrow and then washed prior to binding the monoclonal antibody thereto, which washing step causes a non-discriminant loss of cells including those desired to be enriched. The microspheres and cells then are mixed together to bind the microspheres to the cells via the first and second antibodies. For removing cell populations from blood or bone marrow to enrich the desired population, a sample generally requires preprocessing by density gradients or RBC lysis and then would be mixed with a plurality of the antibody bound microspheres and then placed in a magnetic field. The remaining sample or supernatant containing the population to be enriched is removed while the microspheres are held in the magnetic field.

The magnetic removal procedure presents several problems. The procedure also removes a number of cells non-specifically from other populations during each removal step. The non-specific removal of cells can become more of a problem when a large sample volume is being utilized, such as five (5) ml and larger, which volume then requires a large number of the magnetic microspheres. When the magnetic microspheres then are placed in a magnetic field, non-specific trapping and removal of other non-targeted cells often occurs. This decreases the yield, i.e., the percent of the desired population remaining which is to be enriched. A single removal step results in a varying yield of a relatively low percent with each succeeding removal step, if utilized, also reducing the yield of the population to be enriched. Further, the magnetic microspheres are relatively expensive.

Other methods of positive selection, including antibody labeled surfaces, have been utilized for selecting and hence enriching populations or subpopulations of cells from a mixture of different cell types. These methods usually have antibody covalently attached to a plastic surface or to polymer particles in a column. In general, the mixed cell population is combined with the attached antibody, either by adding them to a column and letting them incubate or by letting them settle onto a surface. These procedures work optimally when the red blood cells (RBC's) and plasma have been initially removed from the mixed cell population by preparation of either a buffy coat or a mononuclear population, obtained by density gradients, followed by washing the cells and combining them with the antibody labeled surface. Both methods also require preparation of the separation system and washing with a buffer prior to use, which with incubation times of thirty to sixty (30–60) minutes with the antibody, results in a procedure which takes a minimum of three hours for the column and flask method. These methods can be used for positive selection for the cell population of interest.

The method and apparatus embodying the invention can be utilized with a variety of immunological reactions, such as immunological reactions involving reactants and cells. Cells are the least structural aggregate of living matter capable of functioning as an independent unit. For example, cells can be human RBC's, WBC's, including the HSC population, cancer or other abnormal cells from tissue, bone marrow, VBM and/or from blood samples from human or animal sources.

As utilized herein, the term "reactant" defines various molecule(s), such as monoclonal or polyclonal antibodies, which detect and react with one or more specific complementary molecule(s), such as antigens, which are on the surface of a cell. Some examples are given below:

| Reactant | Specific Molecule |
| --- | --- |
| Antibody | Antigen |
| Drug | Drug Receptor |
| Hormone | Hormone Receptor |
| Growth Factor | Growth Factor Receptor |
| Lectin | Carbohydrate Molecule |
| Enzyme | Cofactor or Inhibitor |

The reactants couple or bind to the specific molecule(s) on the cells.

It would be desirable to have an effective method of removing one or more populations or subpopulations without effecting the remaining population or populations to be enriched in a sample, such as whole blood, bone marrow or VBM. The technique should obviate the need for gradient centrifugation, specialized cell processors or lysis procedures. The method should be inexpensive, fast, result in a high yield of the population to be enriched and not be restricted in the volume of sample to be acted upon.

SUMMARY OF THE INVENTION

The invention provides a method and apparatus for enriching at least one desired population or subpopulation in a biological fluid sample, such as whole blood or bone marrow, quickly and with a high yield. A plurality of dense, relatively heavy particles having one or more reactants, such as monoclonal or polyclonal antibodies, bound thereto are mixed with the sample. The reactant, such as antibodies bound to the particles are directed at specific molecules on the cells which are not of interest. The particles with the cells bound thereto are allowed to differentially settle by gravity and then the remaining sample supernatant is removed. This enriches the number of remaining cells of interest in the sample supernatant which were not targeted by the particles. The remainder of the sample fluid or supernatant containing the enriched cells then can be removed from the particles with the undesired targeted cells bound thereto. The enriched cells can be utilized or analyzed to determine how many enriched cells remain. The remaining sample or supernatant is removed and can then be utilized with the enriched cell population or subpopulation as is, can have a repeat removal procedure performed to remove more of the same and/or different undesirable cell populations or subpopulations or can be utilized in another type of cell removal procedure to further purify one or more desired cell populations or subpopulations. A preferable particle material of interest can be nickel. The nickel particles preferably can be heated to sterilize the particles. If the sample has been enriched for the desired population and is to be transplanted into a human or other mammal, a magnetic field and washing procedure can be utilized to ensure that all the dense particles have been removed from the sample.

BRIEF DESCRIPTION OF THE DRAWINGS

FIGS. 3A–3C are histograms of bone marrow enriched utilizing prior art techniques;

DETAILED DESCRIPTION OF THE PREFERRED EMBODIMENTS

Figure 1:
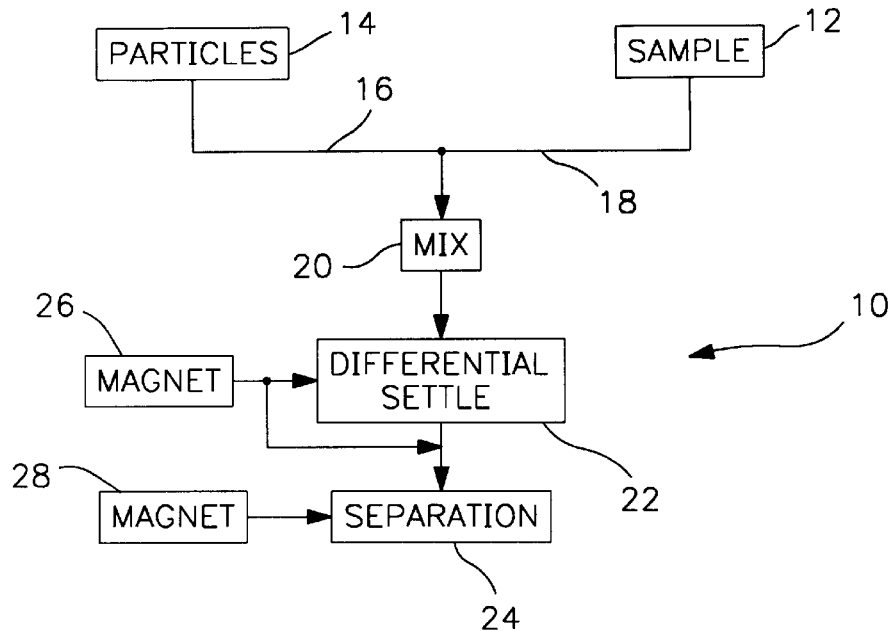
FIG. 1 is a schematic block diagram of a first embodiment of an enrichment technique according to the present invention.

Referring now to FIG. 1, a first embodiment of a cell population or subpopulation enrichment method and apparatus according to the invention is designated generally by the reference numeral 10. The enrichment apparatus 10 includes a fluid sample 12 containing a population or subpopulation to be enriched by removal of one or more undesirable populations or subpopulations. The populations or subpopulations can be a population or subpopulation of cells, such as neutrophils (N's), eosinophils (E's), monocytes (M's), lymphocytes (L's), lymphocyte subsets, immature cells-from stem cells to mature leukocytes, and diseased cells, such as human or animal cancer cells, or biological particles such as platelets (PLT's) found in bone marrow (including VBM and marrow aspirates) or blood (including peripheral and cord blood). The fluid sample can be a biological fluid, including whole blood or a portion thereof, bone marrow or VBM, containing populations or subpopulations, such as described above.

The separation apparatus 10 also includes a source of particles 14. The particles 14 include a reactant, such as for description purposes only, a monoclonal or polyclonal antibody bound thereto, which will bind specifically to selected cells. The antibody can be bound to the particles 14 directly, either covalently or by adsorption, or indirectly via a second antibody in any conventional manner. A plurality of the particles 14 and at least a portion of the sample 12 are combined via respective lines 16 and 18 in a mixing station 20. The combined sample portion and the particles 14 are mixed and then allowed to differentially settle by gravity sedimentation as shown by a block 22. The sample 12 and particles 14 are mixed to facilitate the binding of the particles to the selected cells of interest. The mixing of the sample 12 and the particles 14 is effected to cause the particles 14 to contact the selected cells in the sample 12. An advantage of the dense particles 14 is that they differentially will gravity settle through the sample 12 following mixing without substantial trapping of the non-selected or non-targeted cells to be enriched. During mixing, another advantage of the particles 14, is that the mixing is performed to cause the particles 14 to repeatedly pass or settle through substantially all of the sample to provide cell particle binding without physically damaging the cells with the particles 14. For large volumes, of interest in transplantation procedures, on the order of 100 ml to 3.0 liters, an effective mixing method is to tumble the particles 14 and the sample 12 in an end over end fashion.

Once the particles 14 have been mixed with the sample 12, the particles 14 are allowed to settle to the bottom of a container (not illustrated), then the remaining sample fluid and cells can be separated as illustrated by a block 24. The particles 14 have a density sufficiently greater than the populations in the sample 12, both targeted and non-targeted, that the particles 14 and the targeted populations bound thereto will settle differentially through the sample 12, leaving the unbound/non-targeted enriched populations in suspension. For example, if the sample 12 is a blood sample, the blood cells have a density on the order of 1.05 gm/cc, thus the particles 14 should be substantially more dense than the cells, at least on the order of two (2) to three (3) times more dense than the cells. The remaining sample fluid and cells can be removed for study, further processing, testing or utilization where the selected cells of interest have remained in the supernatant fluid and have been enriched and are not bound to the particles 14. The bound particles 14 and cells also can be removed from the remaining sample fluid for removal of the cells from the particles 14, if desired, for study or utilization of the bound cells where they also are of interest. The remaining fluid with the enriched cells also can be reinfused into a living organism, without the particles and undesirable cells bound thereto, which were eliminated from the sample or fluid.

The apparatus 10 can be an automatic device combining the sample 12 and the particles 14 and moving them between the stations or can be a manual procedure, such as carried out by an operator utilizing a test tube or container for the stations 20, 22 and 24 or can be a combination of the two procedures.

Also, while the settle and separation steps 22 and 24 preferably can be accomplished by gravity separation alone, additional steps can be included, where desired. The particles 14 also can be of a magnetic material. With the magnetic particles 14, a magnet or a magnetic field, illustrated by a block 26, can be applied to the bottom of the container (not illustrated) to accelerate the settling step 22. Additionally, the magnetic field 26 can be maintained or can be applied to the bottom of the container to ensure that the particles 14 remain and are not removed with the enriched supernatant fluid and cells in the separation step 24. The supernatant can be removed and further can be passed by or through a magnetic field 28 to insure that no particle fragments or particles 14 remain in the fluid sample, such as when the sample is to be reinfused into a living organism, such as the human body.

Figure 2:
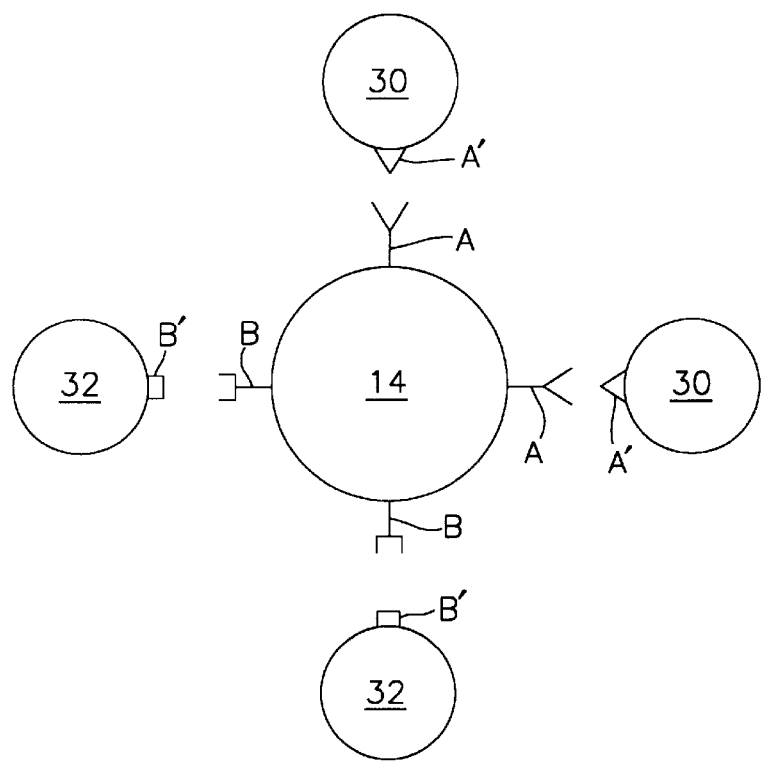
FIG. 2 is a conceptual embodiment of a particle with targeted cells bound thereto in accordance with the present invention.

Referring now to FIG. 2, a conceptual diagram illustrates one particle 14 having two different antibodies A and B bound thereto. For example purposes, a pair of A positive cells 30 are illustrated including at least one antigen A', which specifically will bind with one bound antibody A on the particle 14. A pair of B positive cells 32 also are illustrated including at least one antigen B', which specifically will bind with one bound antibody B on the particle 14. In reality, there would be no particular order to the cell binding and there generally would be an A or a B positive cell blocking the view of the particle 14 on both free sides of the particle 14 (not illustrated). Also, the A & B antibodies on one particle 14 bind to a single cell expressing both the A' and B' antigens. For example, in a normal peripheral blood sample, if the A cell was a CD4 positive cell and the B cell was a CD8 positive cell, then there would be four or five A cells and only one or two B cells bound to the particle 14. This ratio exists since the order of binding correlates approximately to the proportion of cells present. In a normal sample, the ratio of CD4 to CD8 positive cells is about 2 to 1.

Although two different antibodies A and B are described as both bound to the particle 14, each antibody can be bound to separate particles 14 as desired. Also, the separate A and B antibody particles 14 can be added to the sample 12, together, or sequentially in different operations, and one or more additional sets of either or both A or B type particles 14 can be added in sequential operations to eliminate all or substantially all of the A and B positive cells 32 and 34 from the sample 12.

Although no specific particle 14 is critical, a magnetic high density particle 14 is preferable. A particular particle 14, a so-called "dense particle" especially suitable for utilization herein is disclosed in Coulter Corporation's application, entitled METHOD OF SELECTION OF A POPULATION OR SUBPOPULATION OF A SAMPLE, as disclosed in PCT publication No. WO95/28643 published on Oct. 26, 1995. The details of the particles 14 which are set forth hereinafter are disclosed in the PCT application.

One preferable particle 14 is formed from carbonyl nickel, such as nickel powders made by INCO, of Suffern, N.Y., as Nickel Powder Type 123. The particles 14 preferably are made with a nominal diameter of about five (5) to ten (10) microns with a preferable range of three (3) to thirty-five

(35) microns, but not limited thereto. The fines (smaller fragments) are eliminated prior to utilization. The particles 14 are relatively heavy, having a density preferably on the order of two (2) gm/cc up to a density of about nine (9) gm/cc. The density of the particles is selected such that the particles will differentially settle through the sample suspension more rapidly than the cells. Thus, the targeted cells bound to the particles will be gravity separated prior to any significant isolation by settling of the unbound (non-targeted) cells. Clearly, the greater the differences in density between the sample populations and the particles 14, the faster the differential settling will occur. Utilizing the particles 14, gravity settling in a sample portion generally is accomplished in about four (4) minutes, but can be carried out for longer times on the order of six (6) to ten (10) minutes, up to about thirty (30) minutes.

The volumes of the sample fluid vary, depending upon the procedure being performed. For analysis of blood or bone marrow, as little as ten (10) microliters can be utilized, while for clinical transplantations, such as utilizing growth factor stimulated peripheral blood, bone marrow or VBM, the volumes can range from about one hundred (100) milliliters to three (3) liters. In whole blood or bone marrow, many procedures can be utilized, such as stem cell isolation by elimination of the other blood cells by binding them to one or more monoclonal antibodies bound to one or more of the sets of particles 14.

One preferred method of mixing the particles 14 with the sample 12 is to gently tumble the particles 14 and sample mixture end over end for a suitable time period on the order of 4 to 30 minutes, but preferably about 4 to 10 minutes. The mixing causes the particles 14 repeatedly to fall through the sample 12 to bind to the population of interest. This appears preferable, but the familiar roller rocking or stronger mixing procedures can also be effective, if physical damage to the cells of interest by the heavy, dense particles 14 is avoided. One such device can be a test tube holder which rotates slowly to rotate the test tube or similar vessel end over end. This allows a "gentle mixing" of the particles 14 and sample 12 in which the particles 14 mix and settle through a substantial portion of the sample on each rotation allowing the targeted cells to bind to the particles with no apparent physical damage to the cells. The same mixing motion can be obtained by rotating or oscillating the tube back and forth with each end being first on top and then on the bottom, similar to the end over end rotation. The speed of the roller rocker also can be set to effect substantially the same mixing procedure.

One preferred method of labeling the particles 14 with antibody, thus resulting in particles that are both effective in depleting specific subpopulations of cells from a sample mixture, (i.e. whole blood, bone marrow, VBM or mixed cell populations and biological particles) and, due to the density of the particles, also are effective for removal of specific bound cells along with the particles, is set forth hereinafter.

The use of the particles 14 depends both on the density of the particles 14, which allows for rapid settling through a solution and also on the specificity of the selected antibody which allows for attachment of antibody bound particles to specific antigens. The following so-called direct label procedure stipulates the conditions for adsorption of antibody onto the nickel particles 14.

Materials:
1-1 Tris/NaCl Buffer.
1-2 Tris/NaCl/0.2% HSA (Human Serum Albumin) Buffer.
1-3 Monoclonal antibody concentrate.
1-4 Nickel particles, INCO Type 123.

Procedure:
2-1 Determine the amount of the nickel particles 14 that will be utilized by weighing the nickel particles (calculate 1 gm of particles/0.34 m² of particle surface area).
2-2 Heat the particles at 250° C. for 3 hours with mixing periodically, such as every hour and allow the particles to cool before utilization.
2-3 Dilute the appropriate amount of antibody that will be added to the nickel particles 14 into a buffer of Tris/NaCl, pH7.2 (total volume during labeling will be 1 ml/gm of particles).
2-4 Measure the amount of the antibody concentrate and add to the Tris/NaCl buffer to yield a suspension of 1 gm particles/ml of buffer (add antibody at 5 mg/m² particles).
2-5 Place suspension in an appropriate mixer, such as a roller mixer and mix overnight at room temperature.
2-6 Allow the particles to settle to the bottom of the suspension.
2-7 Decant supernatant and replace with the Tris/NaCl buffer to yield a suspension of 3 ml/gm of the particles 14.
2-8 Mix the suspension for an appropriate time, such as 30 minutes, to allow antibody to equilibrate.
2-9 Wash the particles 14 by repeating steps 2–6 to 2–8.
2-10 Allow the particles 14 to settle to the bottom of the suspension.
2-11 Resuspend the particles 14 in the Tris/NaCl/0.2% HSA buffer at 2 ml/gram of particles.
2-12 Mix the suspension for 30 minutes.
2-13 Repeat steps 2–10 to 2–12 an additional two times to block nonspecific binding sites.
2-14 Store the antibody labeled particles at 2–8° C. in the Tris/NaCl/0.2% HSA buffer.

The above procedure also can be utilized to produce particles labeled with polyclonal antibody, such as goat anti-mouse immunoglobulin (GAM). These GAM particles then can be utilized in a so-called indirect antibody labeling method, in which the particles 14 are labeled with desired monoclonal antibodies via binding of the monoclonal antibody to the polyclonal antibody on the particle surface. In this case, labeling is done with 5 ug monoclonal antibody/30 ul GAM particles/ml whole blood or cell suspension.

1. Wash appropriate volume of GAM-nickel particles with Tris/NaCl three times to remove any free GAM.
2. Add the Tris/NaCl buffer along with the selected antibody to the particles (100 ul/30 ul of particle suspension).
3. Incubate on appropriate mixer for 20 minutes at room temperature.
4. Wash the particles to remove unbound antibody.
5. Utilize the particles for depletion of the selected cell population.

It is possible to add more than one antibody to a single GAM particle. An example would be CD14 and CD4 bound together on a particle 14 to deplete M's.

Also, some antibodies do not bind well to particles, such as the nickel particles 14. In that case, to prevent excessive free antibody and potential failure of the binding of the particles to the cell population of interest, the antibodies can be fixed on the particles.

The invention is adapted particularly to bind microspheres to PLT's, and lineage cells specific to WBC populations or RBC populations and other cell populations or subpopulations to be removed from the sample. As utilized herein, WBC subset populations are subsets of a WBC population to which specific monoclonal antibodies can be bound. A nomenclature has been defined for the monoclonal antibodies by the World Health Organization and the International Immunology Society. The monoclonal antibodies are defined by a cluster designation (CD) nomenclature which defines a particular specificity for a cell or group of cells and the monoclonal antibodies specific for that CD group. For example purposes only, some CD groups have been specified in the following table along with the Coulter Corporation antibody designator.

TABLE I

ANTIBODIES UTILIZED FOR PREPARATION OF NICKEL PARTICLES FOR DEPLETION

| PARTICLE LABELS | ANTIBODY/DESIGNATOR |
| --- | --- |
| Platelet | CD41 PLT–1 |
| B cell | CD20 B1 |
|  | CD19 B4 |
| MY | CD14 MY4A |
|  | CD33 MY 9 |
| MT4 | CD2 T11 |
|  | CD5 T1 |
|  | CD7 3A1 |
|  | CD26 TA1 |
| T4 | CD4 T4 |
| T8 | CD8 T8 |
| Myeloid lineage | CD15 KC–48 |
| Class II | I3 and/or I2 |
| Erythroid lineage | KC–16 |
| Stem Cell | CD 34 |
| Dendritic Cell | CD83 HB15 |

For ease of utilization, it has been found that lyophilized particles 14 appear to be as effective as non-lyophilized particles. Lyophilized particles could be utilized in kits or other configurations, since the lyophilized particles 14 eliminate the requirement of maintaining the particles in solution.

In many types of cancer treatment, a patient's marrow is subjected to cytoreductive chemotherapy and radiotherapy, which results in a dearth of PLT's, leukocytes (WBC's) and erythrocytes (RBC's). A majority of the stem cell (HSC) population, which generates these cell populations, is destroyed by the chemicals and/or radiation utilized in such therapeutic protocols. The destroyed cell populations need to rapidly be replaced, because the patient remains at a high risk of life-threatening infection or bleeding. The stem cell or the HSC population, which can be harvested from bone marrow, peripheral blood or cord blood then can be transplanted into the patient after the cytoreductive treatment, which has been found to rapidly regenerate the required WBC and PLT cell populations in many cases.

The successful treatment of a cancer patient, when utilizing autologous hematologic reconstruction (i.e., the utilization of the HSC population harvested from the cancer patient's own bone marrow or blood) is limited by the high risk of cancer recurrence from undetectable and/or non-removed residual tumor cells. For a patient to have a "complete remission", the tumor cells have to be substantially or completely removed from the reintroduced stem cell population. It has been found that hematopoietic stem cells and early progenitor cells express the CD34 antigen on the surface of the cells. Tumor or cancer cells in general, however, do not have cell surface CD34 antigens. Conventional selection techniques for the CD34 positive cell population are work intensive and time-consuming processes, typically requiring a density gradient technique or other cell selection process, (including the utilization of specialized cell processors and RBC lysis) and/or cell washing, thus resulting in nonspecific loss of some of the CD34 positive cell population desired to be enriched, as well as other cell populations which may be desirable to be retained.

The present invention is especially directed toward enriching a so-called "rare event" cell population, such as the CD34 cell population, which population is on the order of only about 1 percent in bone marrow aspirates, 1 to 3 percent in VBM, and less than 1 percent in unstimulated peripheral blood. Other rare event cell populations of interest are natural killer (NK), stromal, dendritic and endothelial cells and osteoblasts. Also, although the major emphasis in all cell population enrichment is directed to human biological samples, other animal/mammal biological samples also can be of interest, such as those from mice, rats, dogs, pigs, cows and primates, among others.

In most types of enrichment processes, the RBC's must be eliminated from the biological sample, such as bone marrow (which typically is contaminated with whole blood) and whole blood. As previously stated, the prior art techniques eliminate the RBC's utilizing either lyse or a density gradient operation. In either case, the cell population of interest also can be effected and/or partially and non-specifically eliminated.

Figure 3C:
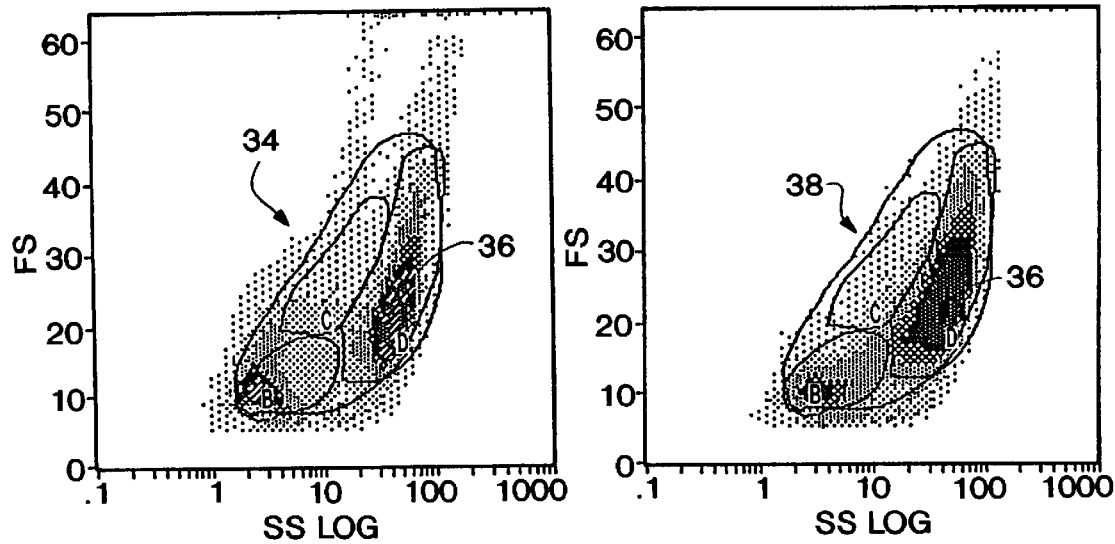

The dense particles 14 were utilized by Applicants to enrich the CD34 population in a VBM or bone marrow without the requirement or utilization of a density gradient operation, providing a significant improvement over the prior art. The present invention thus importantly can be utilized on unprocessed blood or bone marrow samples, but is not limited thereto. Referring now to FIGS. 3A–3C, the prior art techniques of bone marrow enrichment are illustrated utilizing histograms generated by a portion of a bone marrow sample analyzed on a flow cytometer, such as the EPICS XL available from Coulter Corporation, Miami, Fla. Each of the histograms is generated by the data obtained from forward light scatter (FS) and the log of side light scatter (SS LOG) in a conventional manner.

A VBM sample is analyzed in FIG. 3A which results in a multicell population grouping 34. One cell population grouping 36 within the grouping 34, includes mononuclear cells (MNC) and polymorphonuclear (PMN) cells which constitute immature and mature myeloid cells, respectively, and which are desired to be eliminated to enrich the CD34 cell population. The MNC's in the grouping 36 include the immature myeloid progenitor cells in various stages of differentiation. The PMN's include the so-called "segs" or mature N's which have differentiated to the stage where the nucleus begins to segment. The cell grouping 36 is substantially devoid of the CD34 cell population. Utilizing a prior art density gradient technique, here Ficoll-paque, the PMN's and mature RBC's are removed resulting in a cell grouping 38, as illustrated in FIG. 3B. The cell grouping 36 has not been eliminated as can be seen from a comparison of FIG'S. 3A and 3B; therefore, despite removal of the PMN's and the mature RBC's, no significant enrichment of the CD34 cell population has been obtained.

Utilizing an average of the results from flow cytometric analysis of seven (7) different bone marrow samples, labeled with dye conjugated anti-CD34 specific monoclonal antibody, the CD34 cell population is 1.9±0.3 percent of the cell grouping 34. After the density gradient operation, the CD34 cell population is 3.5±0.6 percent of the cell grouping 38. The ficoll separated cells are processed over a further density gradient, metrizamide, thus resulting in a cell grouping 40 as illustrated in FIG. 3C. This gradient step enriches for the low buoyant density cells, known to contain the CD34 cell population, from the ficoll gradient sample illustrated in FIG. 3B. However, the cell grouping 36 containing myeloid progenitor (MNC's) still clearly is evident and the CD34 cell population is only 3.9±1.2 percent of the cell grouping 40. Clearly the CD34 cell population has not been enriched to the desired degree by these prior art techniques.

Figure 3C:
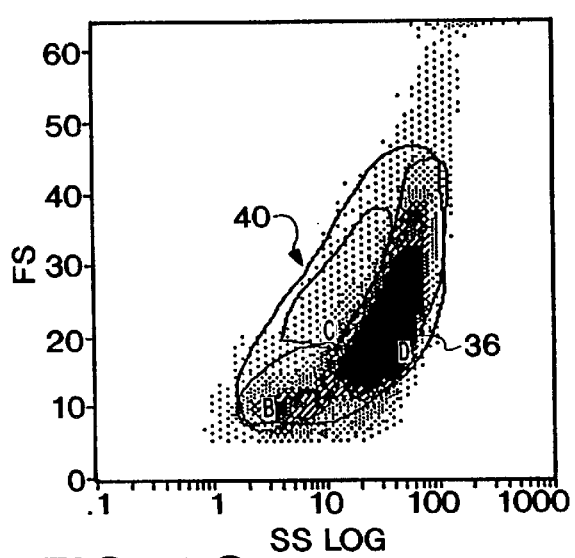
Figure 4A:
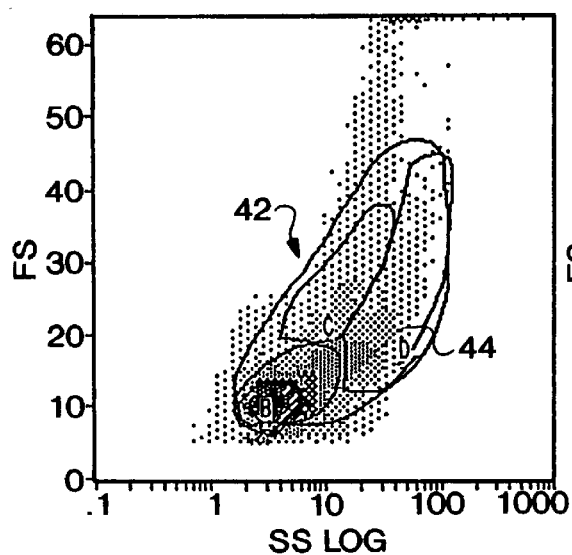
FIGS. 4A–4C are histograms of enriched bone marrow
Figure 4B:
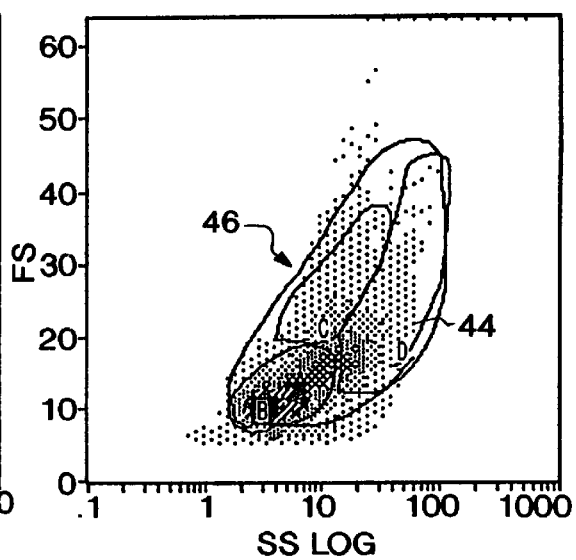
Figure 4C:
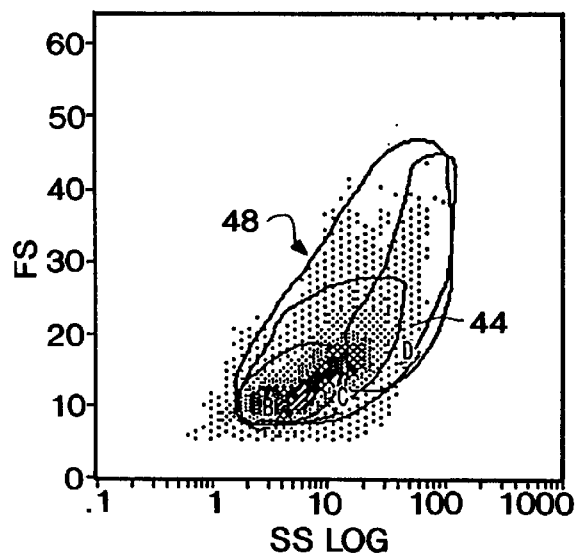

Applicants, upon review of the data from the density gradient results illustrated in FIGS. 3A–3C, believed that removal of the myeloid cells contained in the cell grouping 36 should enrich for the CD34 cell population of interest, since the cell grouping 36 is substantially devoid of CD34 cells. Another portion of the bone marrow utilized in FIGS. 3A–3C, was utilized and generated the data illustrated in FIGS. 4A–4C. The bone marrow sample was combined with a plurality of particles 14, having a myeloid lineage positive antibody (CD15) bound thereto. One such exemplary N and E specific antibody is disclosed in U.S. Pat. No. 4,931,395, assigned to Coulter Corporation, incorporated herein by reference and sold by Coulter Corporation as a KC48 antibody. Removal of the CD15 cell population from the bone marrow samples, represented in FIGS. 3A–3C, with the particles 14 having the CD15 antibody bound thereto, resulted in the cell population groupings 42 (FIG. 4A), 46 (FIG. 4B), 48 (FIG. 4C); these cell population groupings were contained in the supernatant after the separation step 24. As can be seen by comparing FIGS. 3 and 4, a cell population grouping 44 has had a significant number of cells removed from the comparable cell population grouping 36. With regard to the CD34 positive HSC, removal of the CD15 cell population resulted in an enrichment from 1.0 to 3.9% for the whole bone marrow (FIGS. 3A and 4A), 2.4 to 6.5% for the ficoll gradient enriched cell population (FIG. 3B and 4B), and 4.2 to 12.5% for the metrizamide enriched cell population (FIGS. 3C and 4C). Therefore, in order to achieve minimal enrichment of HSC, two density gradient separation procedures were required, followed by removal of the CD15 cell population. This process was lengthy, unwieldy, and costly and the extensive manipulation involved resulted in poor cell recovery.

Figure 5A:
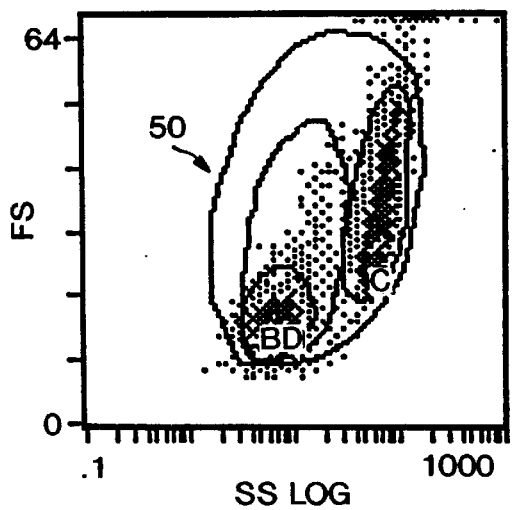
FIGS. 5A–5D are histograms of enriched bone marrow
Figure 5B:
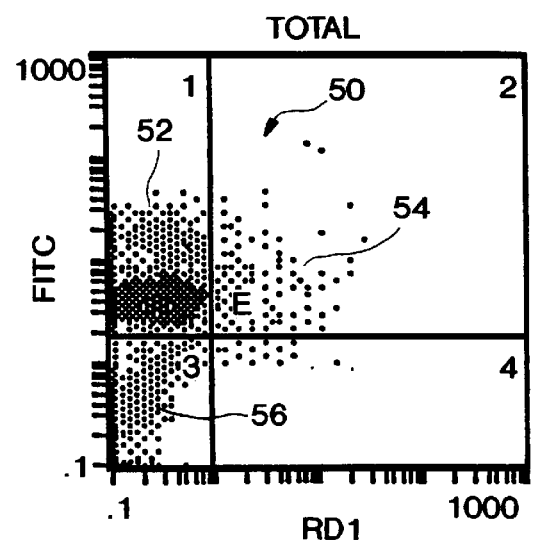

After further investigation, Applicants discovered that at least one of the significant remaining contaminants were nucleated RBC's. This was confirmed utilizing a CD45 specific antibody, which identifies only the WBC's, including the CD34 cell population. This conclusion was confirmed by Applicants from data illustrated in FIGS. 5A–5C. FIGS. 5A and 5B are two views of an unmanipulated bone marrow sample obtained on a flow cytometer. The histograms generated from one bone marrow sample illustrate the light scattering characteristics (FS vs. log SS) exemplified by a cell population grouping 50 as illustrated in FIG. 5A, as well as the results of analysis with two different fluorescent staining reagents, as illustrated in FIG. 5B. A CD45 specific FITC reagent was utilized which stains all leukocytes, including the HSC population, and a CD34 specific RD1 or PE reagent was utilized which stains only CD34 positive cells; both of which can be purchased from Coulter Corporation. FIG. 5B is divided into four segments or Quadrants 1, 2, 3, and 4, as numbered in the FIG. Quadrant 1 contains a cell grouping which is CD45 positive WBC's, excluding the CD34 population. Quadrant 2 contains the CD34 cell grouping. Quadrants 1 and 2 contain the total WBC population, while quadrants 3 and 4 contain the non-WBC cell population. Quadrant 3 contains a cell grouping 56, which is both CD45 and CD34 negative. Quadrant 4 generally could contain any cells which are positive to CD34 and are not WBC's. The few cells in quadrant 4 generally are believed to represent noise. The CD34 cell population grouping 54 is 4.5 percent of the total cell grouping 50 and is 7.0 percent of the total WBC population in quadrants 1 and 2, as determined by dividing the number of CD34 cells in Quadrant 2 by the total number of WBC cells in Quadrants 1 and 2.

Figure 5C:
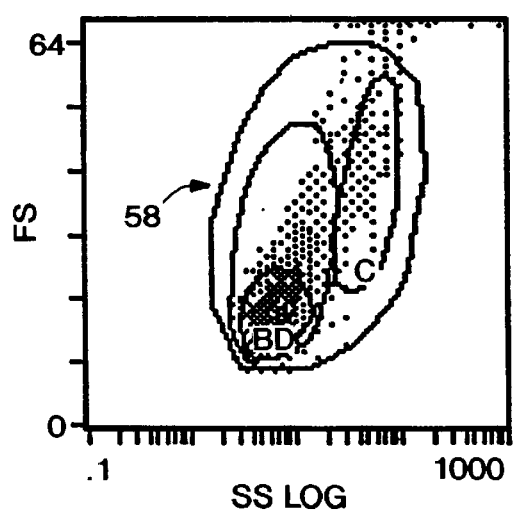
Figure 5D:
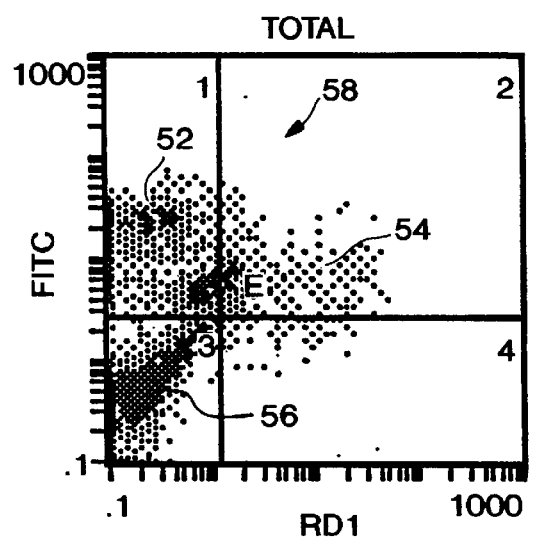

A removal step utilizing CD15 positive particles 14 then is performed on the sample resulting in a cell population grouping 58 as illustrated in FIG. 5C. This decreased the WBC cell population grouping 52 from 65 percent in FIG. 5B to 45 percent in FIG. 5D. The CD34 cell population grouping 54 increased to 10.8 percent of the total and 24.1 percent of the WBC's. The cell population grouping 56 at the same time increased from 35 percent of the cell population grouping 50 to 54 percent of the cell population grouping 58. This contaminating cell population grouping 56 was identified by Applicants as mainly consisting of nucleated RBC's, which are not removed by the prior art ficoll-paque density gradient techniques.

Figure 6A:
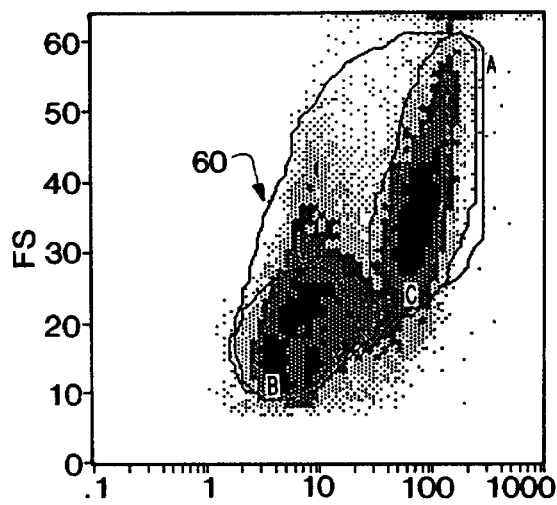
FIGS. 6A–6F are histograms of enriched bone marrow
Figure 6B:
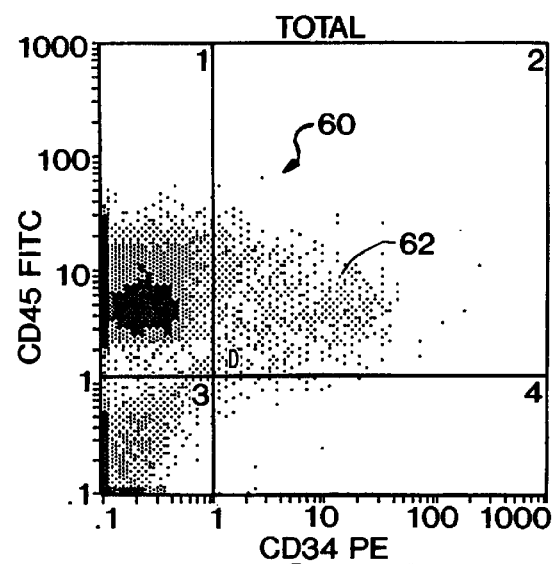
Figure 6C:
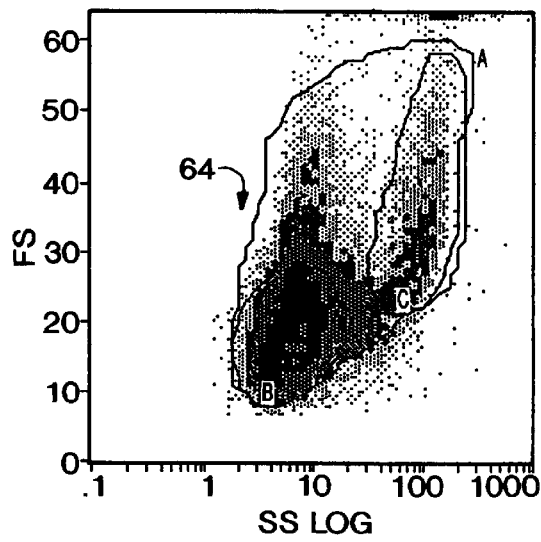
Figure 6D:
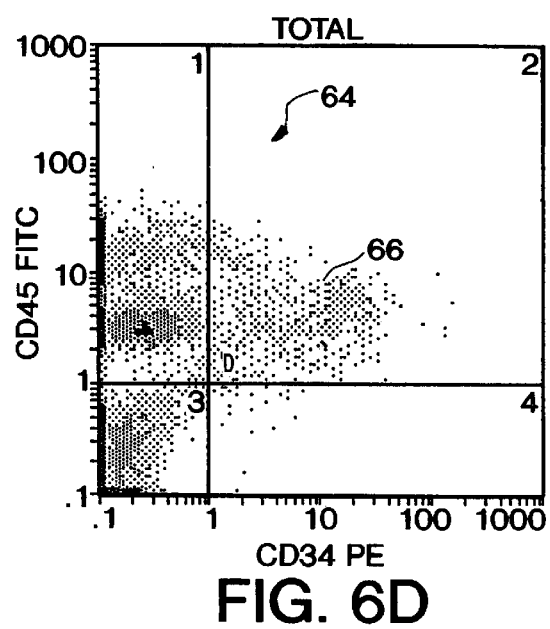

This contaminant identification was confirmed by another bone marrow sample operated on and analyzed as illustrated in FIGS. 6A–6F. This bone marrow sample included a cell population grouping 60 as illustrated in FIG. 6A, which included a CD34 positive cell grouping 62 as illustrated in FIG. 6B. The CD45 cell population 62 was 5.2 percent of the total cell population grouping 60 with the CD34 cell grouping 62 being 9.1 percent of the WBC's. A first CD15 removal step was then performed as illustrated in FIGS. 6C and 6D, resulting in a cell population grouping 64. The cell population grouping 64 includes a WBC cell population grouping 66, which constitutes 6.8 percent of the total cell population 64 and is 21.7 percent of the WBC cell population. Clearly the CD34 cell population 66 has been enriched with respect to the WBC population, however, the contamination illustrated in Quadrant 3 prevents the CD34 cell population 66 from being 21.7 percent of the total cell population grouping 64.

Figure 6E:
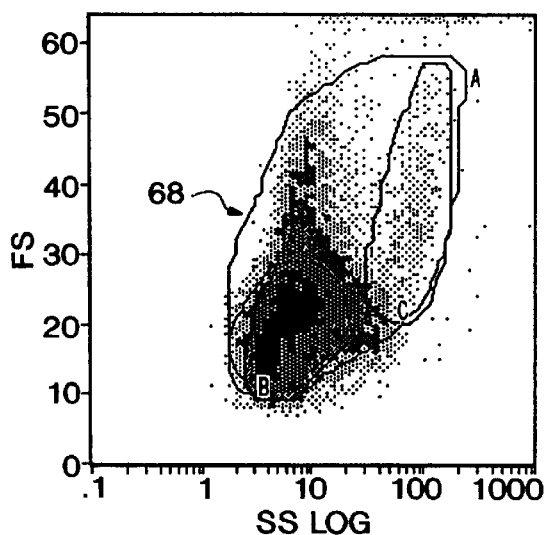
Figure 6F:
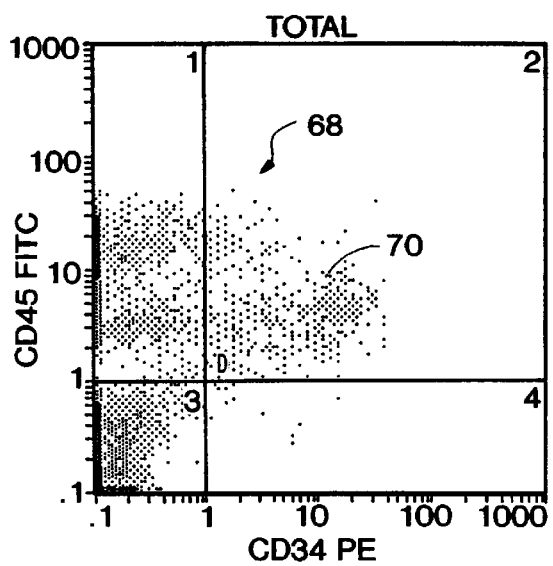

In an effort to further remove contaminants, another CD15 depletion step is performed resulting in a cell population grouping 68 as illustrated in FIGS. 6E–6F. This step produces a WBC cell population grouping 70 which is 5.2 percent of the cell population grouping 68 and which is 23.1 percent of the WBC cell population. The CD34 positive cells as a percentage of the total cell population grouping 68, has actually decreased to 5.2 percent, confirming that the cell population grouping 68 is contaminated with other cells.

Figure 7A:
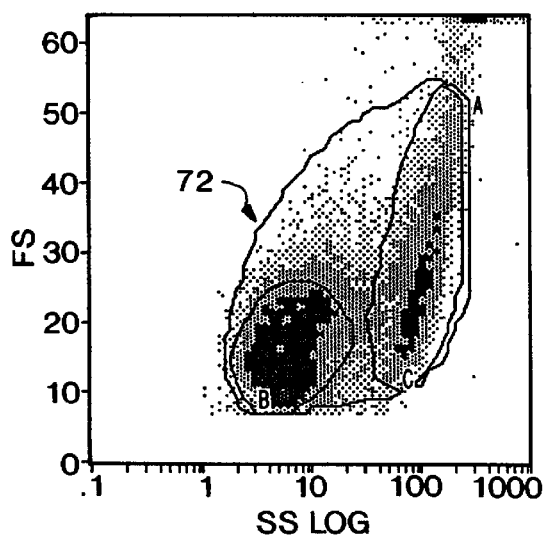
FIGS. 7A–7D are histograms of enriched bone marrow
Figure 7B:
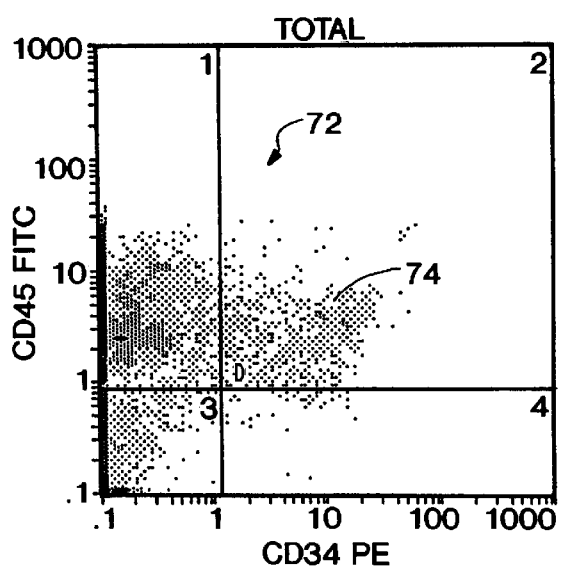
Figure 7C:
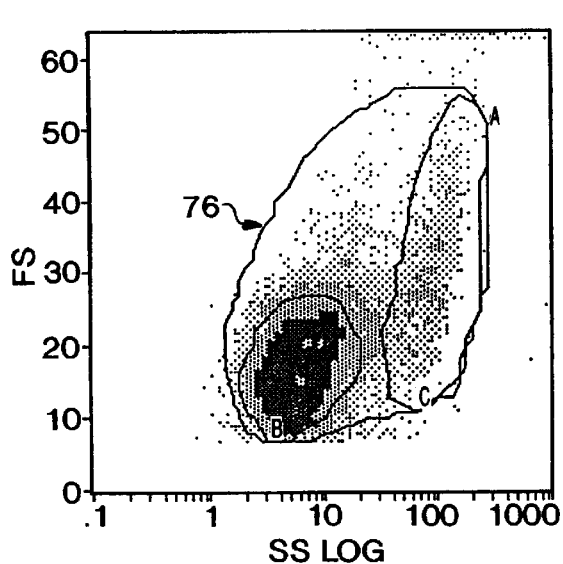
Figure 7D:
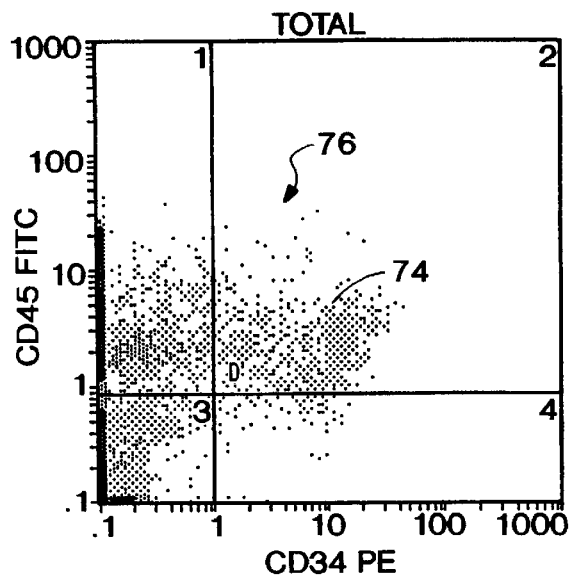

Another confirmation of the contamination was performed by repeating the CD15 removal step as was illustrated in FIGS. 5A–5C. The results of this confirmation bone marrow sample obtained from another patient, are illustrated in FIGS. 7A–7D. A cell population grouping 72 is analyzed before the CD15 removal as illustrated in FIG. 7A and includes a WBC cell grouping 74, illustrated in FIG. 7B, which includes a CD34 population that constitutes 4.0 percent of the cell population grouping 42 and which is 8.1 percent of the WBC's. The CD 15 removal then is performed, resulting in a cell population grouping 76, which includes a CD34 cell population 74 that is 5.2 percent of the cell population grouping 76 and 18.3 percent of the WBC's.

Figure 8A:
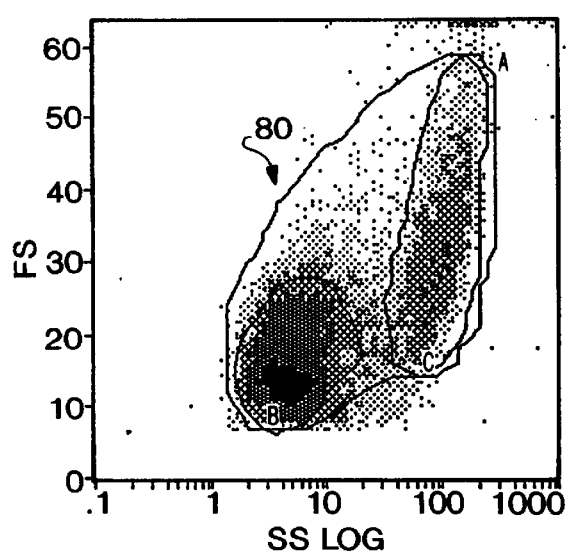
FIGS. 8A–8F are histograms of enriched bone marrow
Figure 8B:
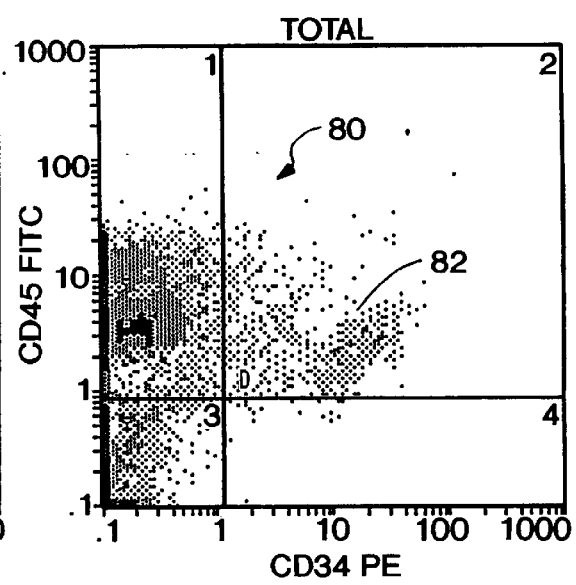
Figure 8C:
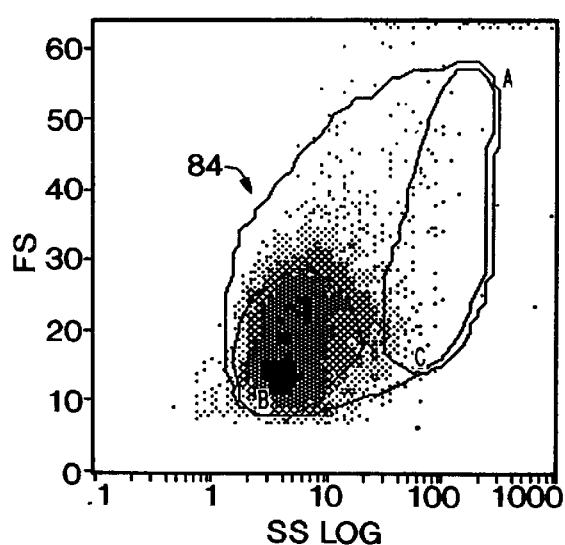
Figure 8D:
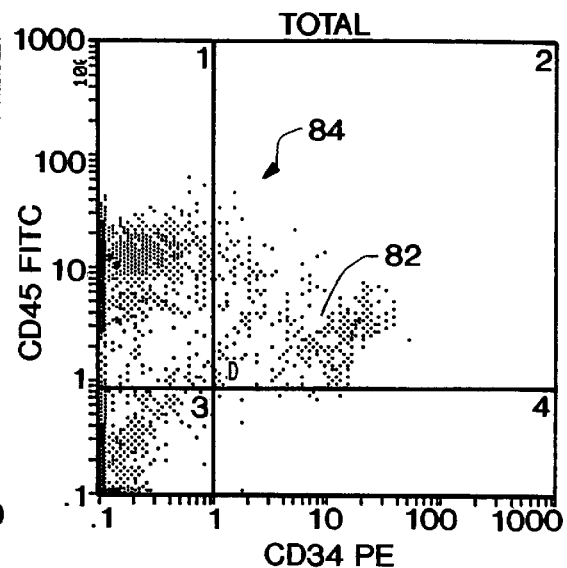
Figure 8E:
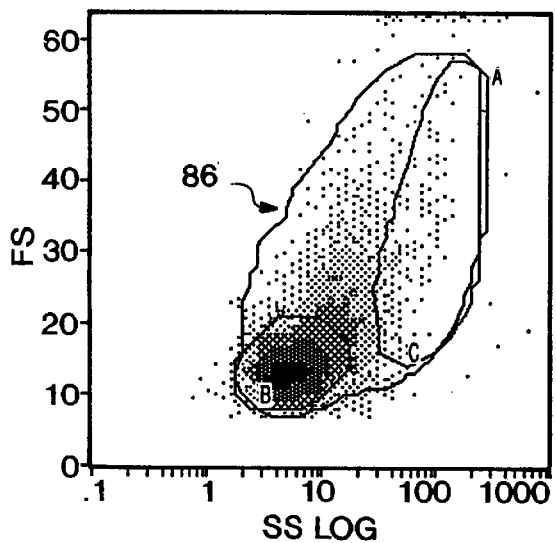
Figure 8F:
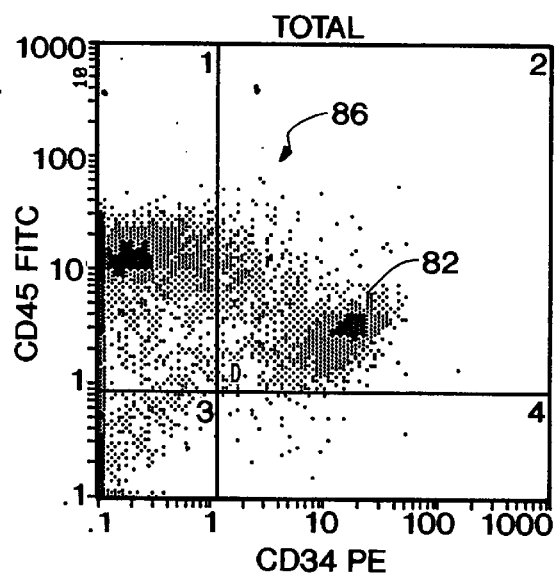

A further experiment then was performed by Applicants to attempt to remove the contaminating population as illustrated in FIGS. 8A–8F. Another bone marrow sample yields a cell population grouping 80 as illustrated in FIGS. 8A and 8B. The cell population grouping 80 includes a CD34 cell population 82 which is 4.6 percent of the cell population grouping 80 and 10.8 percent of the WBC's. A CD15 removal step then is performed, which leaves a cell population grouping 84 after the separation step 24, as illustrated in FIGS. 8C–8D. The CD34 cell population 82 is slightly enhanced, being increased to 11.5 percent of the WBC cell population, but the CD34 cell population has decreased to 3.7 percent of the total cell population grouping 84. The CD15 removed bone marrow sample then is operated on by a ficoll density gradient step to produce a cell population grouping 86 as illustrated in FIGS. 8E–8F. The gradient removal step enriches the CD34 population 82 to 15.9 percent of the cell population 86 and 19.3 percent of the WBC's. Clearly, the density gradient step removed a large amount of the contaminating cells for Quadrant 3. Since a density gradient removal step is undesirable, and since the contaminating cell population was analyzed on a conventional smear on a slide and residual (unremoved) nucleated RBC's were confirmed as part of the undesirable population, Applicants investigated alternate techniques of RBC removal.

Referring now to FIGS. 9A–10F, the removal of the contaminating RBC's, including the nucleated RBC's, utilizing the particles 14 having an erythroid lineage antibody bound thereto is illustrated. One particular erythroid lineage specific antibody is disclosed in Coulter Corporation's U.S. Pat. No. 4,752,563, which is incorporated herein by reference and is sold by Coulter Corporation as a KC16 antibody.

Figure 9A:
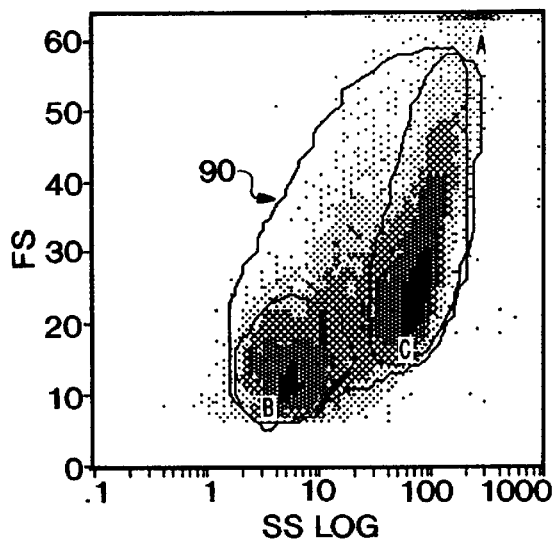
FIGS. 9A–9F and 10A–10F are histograms illustrating the results of bone marrow enrichment obtained with the present invention.
Figure 9B:
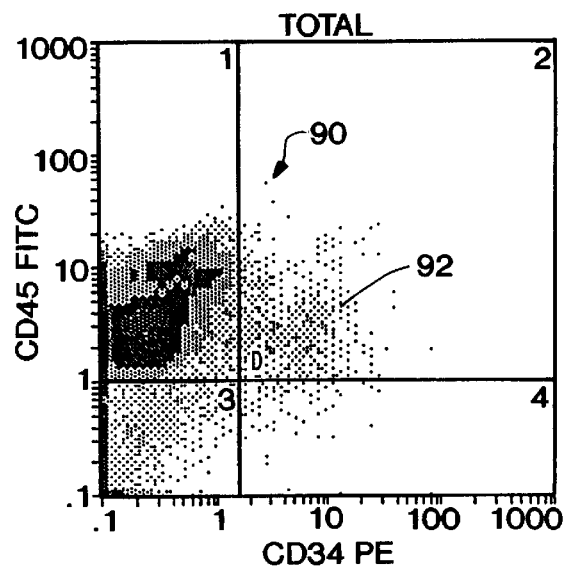
Figure 9C:
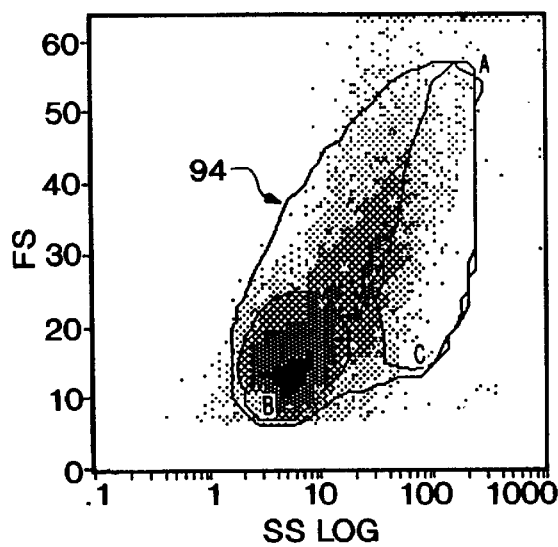
Figure 9D:
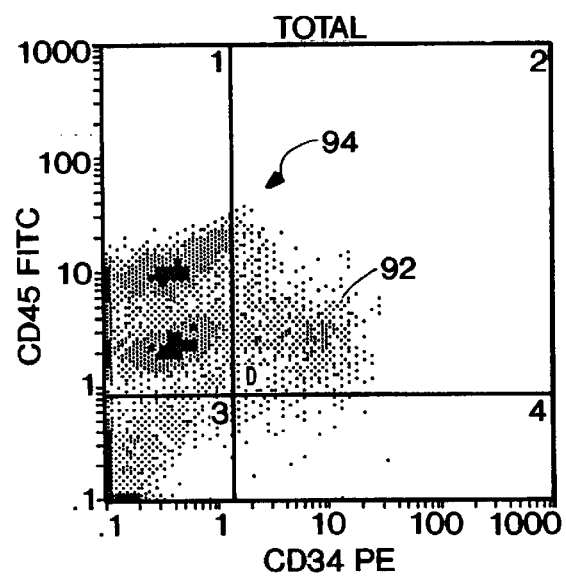
Figure 9E:
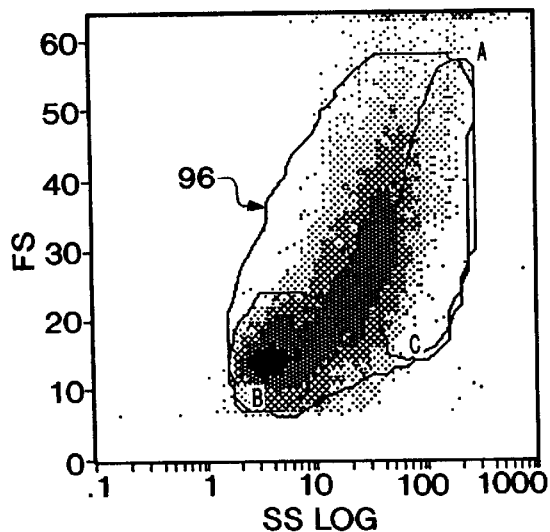
Figure 9F:
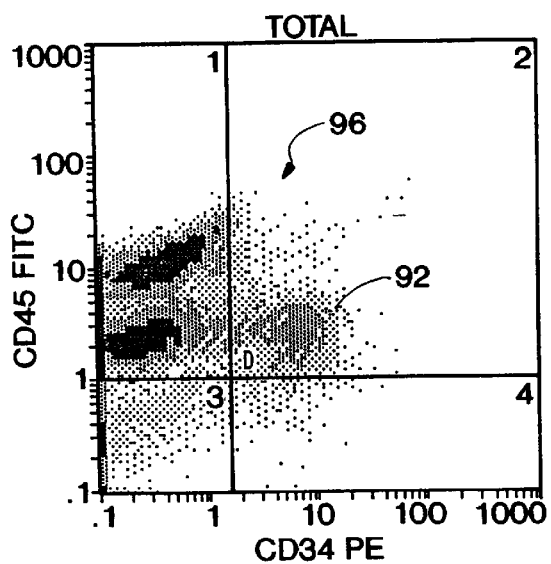

A bone marrow sample yields a cell population grouping 90 as illustrated in FIGS. 9A and 9B. The cell population grouping 90 includes an HSC or CD34 cell population grouping 92, which is 4.4 percent of the total cell population grouping 90 and 9.3 percent of the WBC population. A CD15 or myeloid lineage removal step then is performed, which leaves a cell population group 94 after the separation step 24, as illustrated in FIGS. 9C and 9D. The CD34 cell population grouping 82 is enriched to 5.5 percent of the total cell population grouping 94 and 24.8 percent of the WBC population. An erythroid lineage removal step then is performed, which leaves a cell population grouping 96, as illustrated in FIGS. 9E and 9F. The CD34 cell population group 82 is further enriched to 20.6 percent of the total remaining cell population grouping 96. Thus, the CD34 cell population 82 has been enriched, but as can be seen from Quadrant 1 of FIG. 9F, the major remaining contaminants now appear to be other WBC populations. Although not illustrated, the percentage of erythroid lineage positive cells in the cell grouping 90, 94 and 96 respectively are 7.3, 20.6 and 0.7 percent.

Figure 10A:
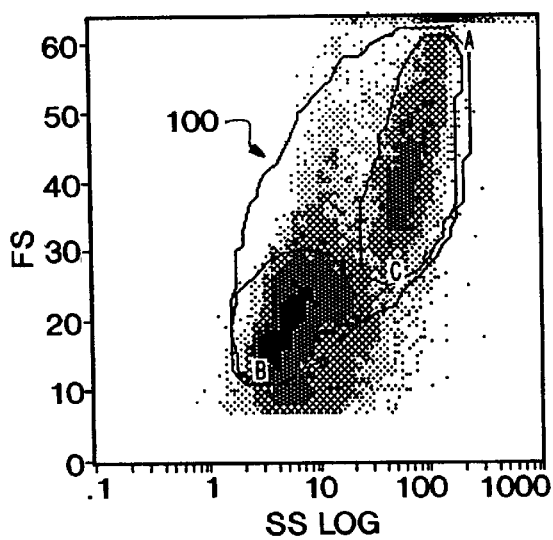
Figure 10B:
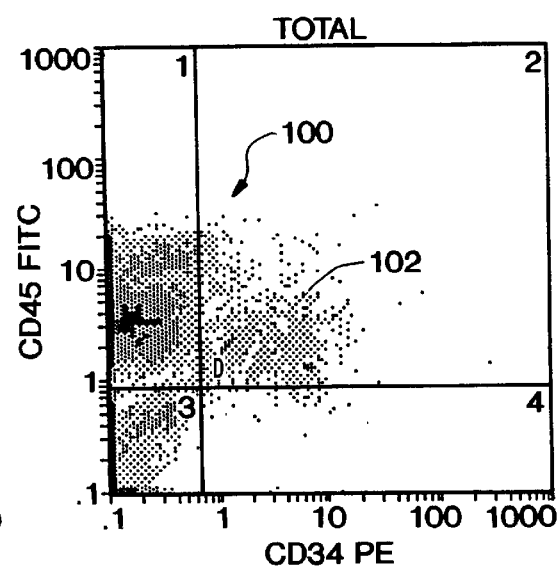
Figure 10C:
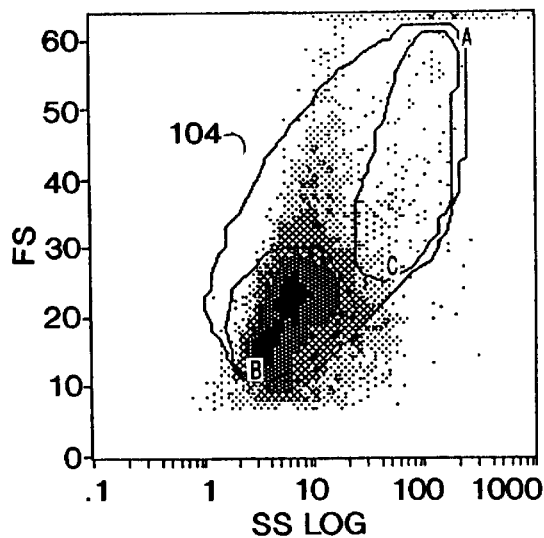
Figure 10D:
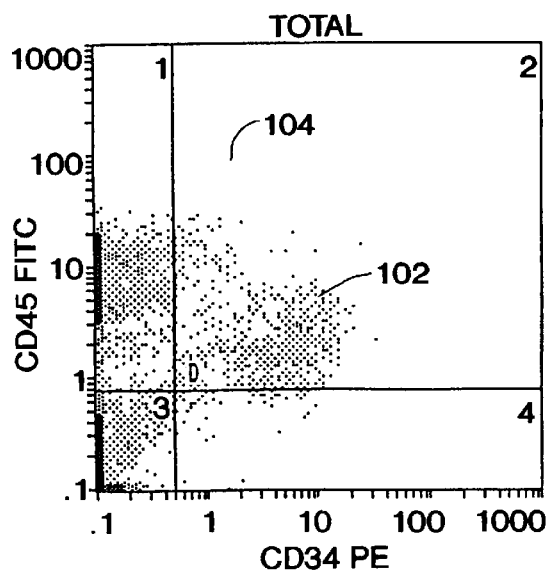
Figure 10E:
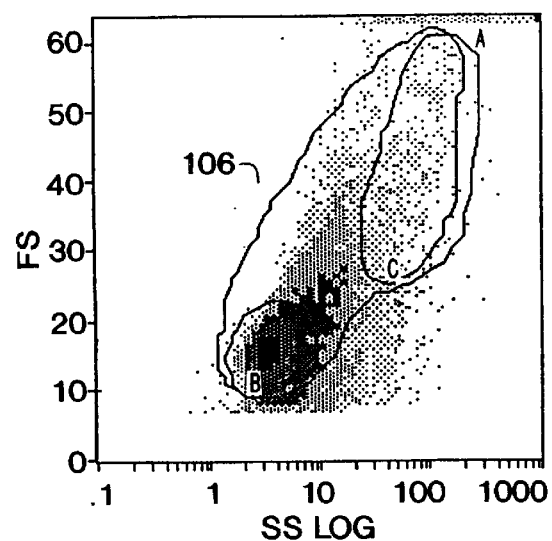
Figure 10F:
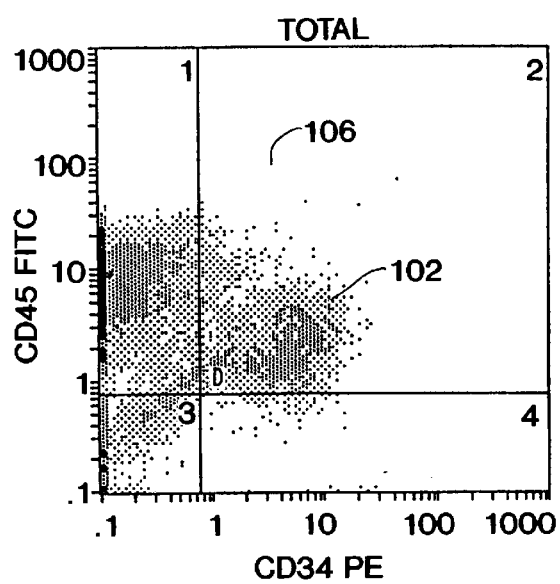

The enriched HSC results illustrated by the bone marrow sample illustrated in FIG. 9 was confirmed by another bone marrow sample as illustrated in FIGS. 10A–10F. Again, the bone marrow sample yields initial cell population groupings 100 as illustrated in FIGS. 10A and 10B. The cell population grouping 100 includes a CD34 cell population grouping 102, which is 5.2 percent of the total cell population grouping 100 and 11.3 percent of the WBC population. A CD15 myeloid lineage removal step then is performed, which leaves a cell population grouping 104 after the separation step 24, as illustrated in FIGS. 10C and 10D. The CD34 cell population grouping is enriched to 5.5 percent of the total cell population grouping 104 and 22.6 percent of the WBC population. An erythroid lineage removal step then is performed, which leaves a cell population group 106, as illustrated in FIGS. 10E and 10F. The CD34 cell population group 102 is enriched to 16.2 percent of the total cell population group 106, but is less than the calculated 18.4 percent of the WBC population. The percentage of erythroid lineage positive cells in the grouping 100, 104 and 106; respectively is 16.1, 35.1 and 0.4 percent.

The technique of the present invention takes advantage of substrates which can be utilized, in combination with the dense particle technology, to remove the vast majority of non-HSC populations from various cell preparations. Mature and immature populations of myeloid cells and RBC's (mature and nucleated RBC's) are eliminated, thus resulting in enrichment of HSC from a starting percentage of 1–3% to approximately 20%, with a high cell recovery. Gradient fractionation, specialized centrifugation procedures, RBC lysis, and column/panning procedures are not required. In addition to rapid enrichment for the critical HSC, this technique allows for the enrichment of other rare event cell population types, which have tremendous potential for therapeutic application, in the event that procedures for rapid and efficient isolation, such as that described herein, are developed to enrich for them. Among these cell types are stromal cells, osteoblasts, and endothelial cells.

Once enrichment for HSC has been achieved, as illustrated in FIGS. 9 and 10, currently marketed technologies for positive or negative selection can be employed to further enrich for the CD34 positive HSC. Alternatively, and preferably, the dense particle technology can be employed to rapidly, and with great recovery of non-targeted cell populations, deplete specific cell types. For example, the vast majority of the remaining cells are T, B, and NK cells, as well as monocytes, and reagents specific for these cells can be used in conjunction with the dense particles to eliminate them. Positive selection can then be employed to obtain the rare event cell types which remain. As an example, CD34 can be utilized to recover the HSC; anti-factor VIII or sENDO-1 specific monoclonal antibodies can be employed for recovery of endothelial cells, STRO-1 for stromal cells, and anti-osteocalcin or anti-alkaline phosphatase monoclonal antibodies can be utilized to recover osteoblasts.

Figure 11:
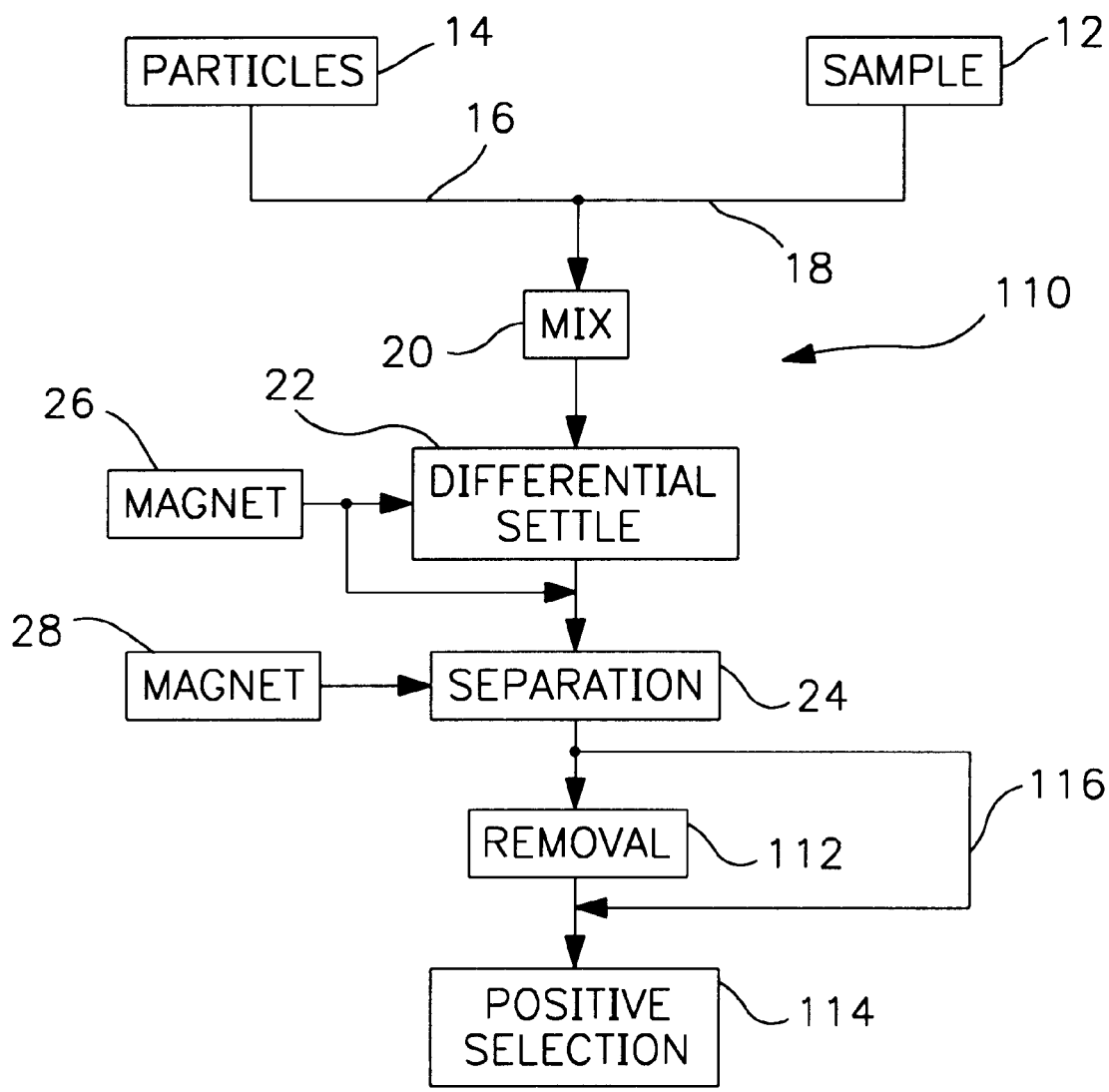
FIG. 11 is a schematic block diagram of another embodiment of an enrichment technique of the present invention.

Further enrichment of the CD34 population is illustrated, referring to FIG. 11. A separation and enrichment apparatus 110 includes the identical steps and elements 12–28 as described with regard to the apparatus 10 in FIG. 1. As previously described, with regard to FIG. 6, a second removal step 112 can be performed. The removal step 112 can include removal of the residual population of a previously removed population, such as another CD15 removal step. Additionally, other populations could be removed with the appropriate antibody such as CD4 or other antibodies positive to M's or B cells or PLT's, as desired or required. Further, since the CD34 population is now one of the major populations, the CD34 population can be removed to enrich for one of the other rare event cells much as dendritic, stromal, endothelial or osteoblast cells.

Also, as previously noted, a positive cell population selection step 114 can be performed to obtain a further enriched population such as the CD34 population. The step 114 can be performed directly after the separation step 24 or after the additional removal step 112 as indicated by the lines 116 and 118, respectively.

When the starting cell number is low, currently existing technologies can be highly effective for the enrichment of rare event cell types; however, when the procedures are scaled up to allow for clinical scale enrichment of, for example HSC, recovery generally drops from 95 to 60%, and the cells must endure a lot of manipulation. Unlike these processes, the technique of the present invention allows for efficient scale up and rapid debulking of undesired populations, without the need for sacrificing ease of use and increasing sample processing time.

As reported by researchers at the University of Texas Southwestern Medical Center, Dallas, Tex., in the *Journal of Immunological Methods* 175(1994)p.247–257, utilization of a positive selection, so-called immunoaffinity column on a peripheral blood mononuclear cell sample (PBMC), obtained after density gradient separation of whole blood to remove the RBC's and PMN's, enabled them to obtain a CD4 positive cell selection of ninety-five (95) percent to ninety-nine (99) percent. The high purity obtained was a direct result of the pre-procesing step, which pre-enriched the CD4 positive cell population to 40% of the PBMC's, thus enhancing the efficacy of the positive selection step. The positive selection step would also greatly enrich an enriched population from the supernantant obtained by the technique of the present invention.

Many modifications and variations of the present invention are possible in light of the above teachings. It is therefore to be understood that within the scope of the appended claims, the invention may be practiced otherwise than as specifically described.

What is claimed is:

1. An improved method for enrichment of one or more desired cell populations in a fluid sample comprising removing undesired erythroid lineage cells and one or more undesired cell populations other than said erythroid lineage cells without cell lysis or density gradient fractionation, said sample comprising a portion of bone marrow, vertebral body marrow (VBM) or blood, wherein said undesired erythroid lineage cells and undesired cell populations other than said erythroid lineage cells comprise a majority of the cells in said fluid sample, said method comprising:

providing a plurality of particles having a density at least twice the density of cells in said sample, said particles having bound thereto one or more reactants which specifically bind to said erythroid lineage cells and one or more reactants which specifically bind to said one or more undesired cell populations;

mixing said sample with said particles to bind said particles to said erythroid lineage cells and said one or more undesired cell populations to form particles with undesired cells bound thereto;

differentially gravity settling said particles in said sample, wherein said settled particles comprise particles with undesired cells bound thereto; and separating at least a portion of the resultant supernatant comprising said one or more desired cell populations from said settled particles.

2. The method of claim 1, wherein one of said desired cell populations is enriched at least 2.4-fold.

3. The method of claim 1, wherein one of said desired cell populations is enriched at least 3.7-fold.

4. The method of claim 1, wherein one of said desired cell populations is enriched 2.4-fold to 20-fold.

5. The method of claim 1, wherein said desired cell populations comprise one or more rare event cell populations.

6. The method of claim 5, wherein said one or more rare event cell populations comprise CD34 positive hematopoietic stem cells.

7. The method of claim 5, wherein said one or more rare event cell population is selected from the group consisting of natural killer cells, stromal cells, dendritic cells, osteoblasts, or endothelial cells.

8. The method of claim 1, wherein one of said undesired cell population comprises myeloid lineage cells.

9. The method of claim 8, wherein said reactants are antibodies and wherein a first antibody is capable of specifically binding erythroid lineage cells and a second antibody is capable of specifically binding myeloid lineage cells.

10. The method of claim 9, wherein each of said particles has both said first and second antibodies bound.

11. The method of claim 9, wherein said second antibody is capable of specifically binding CD15 cells.

12. The method of claim 11, wherein said first antibody is KC-16 and said second antibody is KC-48.

13. The method of claim 9, wherein said plurality of particles comprise first particles having said first antibody bound and second particles having said second antibody bound.

14. The method of claim 1, wherein said plurality of particles comprise first particles having bound thereto one or more of said reactants which specifically bind to erythroid lineage cells and second particles having bound thereto one or more of said reactants which specifically bind to said undesired cell populations.

15. The method of claims 13 or 14, further comprising mixing and settling said first particles in said sample separately and sequentially from mixing and settling said second particles in said sample.

16. The method of claims 13 or 14, wherein said first and second particles are mixed together with said sample.

17. The method of claim 1, wherein said erythroid lineage cells comprise nucleated red blood cells.

18. The method of claim 1, wherein said reactants which specifically bind to said one or more undesired cell populations comprise one or more antibodies.

19. The method of claim 1, wherein said one or more reactants which specifically bind to said erythroid lineage cells comprise one or more antibodies capable of specifically binding erythroid lineage cells.

20. The method of claim 19, wherein said antibody is KC-16.

21. The method of claim 1, wherein one of said undesired cell populations comprise platelets.

22. The method of claim 1, wherein said particles have a diameter from about 3 to 35 microns.

23. The method of claim 22, wherein said particles have a diameter of about 5–10 microns.

24. The method of claim 1, wherein said particles have a density of about 2 g/cm$^3$ or greater.

25. The method of claim 24, wherein said particles have a density of about 9 g/cm$^3$.

26. The method of claim 1, wherein said particles have a density of two to three times the density of cells in said fluid sample.

27. The method of claim 1, wherein said particles are nickel.

28. The method of claim 1, wherein said mixing is carried out for about 4 to 30 minutes.

29. The method of claim 28, wherein said mixing is carried out for about 4 minutes.

30. The method of claim 1, wherein said gravity settling is carried out for about 4 minutes to 30 minutes.

31. The method of claim 30, wherein said gravity settling is carried out for about 4 minutes.

32. The method of claim 1, wherein said mixing, settling and separating steps are repeated at least once, resulting in at least a second resultant supernatant.

33. The method of claim 32, further comprising positively selecting said enriched cell population from said second resultant supernatant.

34. The method of claim 1, further comprising positively selecting said enriched cell population from said resultant supernatant.

35. The method of claim 1, further comprising removing at least a third undesired cell population from said supernatant.

36. The method of claim 1, wherein said mixing is effected by tumbling said sample and said particles end-over-end.

37. An improved method for enriching CD34 positive hematopoietic stem cells in a fluid sample comprising removing erythroid lineage cells and one or more undesired cell populations other than said erythroid lineage cells without cell lysis or fractionation of said sample in a fluid having a density greater than the density of said CD34 positive hematopoietic stem cells, said sample being a portion of bone marrow or vertebral body marrow, wherein said undesired erythroid lineage cells and undesired cell populations other than said erythroid lineage cells comprise a majority of the cells in said fluid sample, said method comprising:

- providing a plurality of particles having a density sufficient to provide differential gravity settling, said particles having bound thereto one or more reactants, wherein a first reactant is capable of specifically binding to said erythroid lineage cells, and wherein a second reactant is capable of specifically binding to cells of a first preselected population to be removed from said sample; said first preselected population being cells of myeloid lineage;
- mixing a portion of said sample having a volume of at least one hundred milliliters with said particles to bind said particles to said erythroid lineage cells and cells of said preselected population;
- differential gravity settling said particles with said bound cells in said sample portion; and
- separating at least a portion of the resultant supernatant of said sample portion including said CD34 positive hematopoietic stem cells from said settled particles.

38. An improved method for enriching CD34 positive hematopoietic stem cells in a fluid sample comprising removing erythroid lineage cells and one or more undesired cell populations other than said erythroid lineage cells without cell lysis or fractionation of said sample in a fluid having a density greater than the density of said CD34 positive hematopoietic stem cells, said sample being a portion of blood, wherein said undesired erythroid lineage cells and undesired cell populations other than said erythroid lineage cells comprise a majority of the cells in said fluid sample, said method comprising:

- providing a plurality of particles having a density sufficient to provide differential gravity settling, said particles having bound thereto one or more reactants, wherein a first reactant is capable of specifically binding to said erythroid lineage cells, and wherein a second reactant is capable of specifically binding to cells of a first preselected population to be removed from said sample; said first preselected population being cells of myeloid lineage;
- mixing a portion of said sample having a volume of at least one hundred milliliters with said particles to bind said particles to said erythroid lineage cells and cells of said preselected population;
- differential gravity settling said particles with said bound cells in said sample portion; and
- separating at least a portion of the resultant supernatant of said sample portion including said CD34 positive hematopoietic stem cells from said settled particles.

* * * * *